(12) United States Patent
Doods et al.

(10) Patent No.: US 7,807,666 B2
(45) Date of Patent: *Oct. 5, 2010

(54) CGRP ANTAGONISTS

(75) Inventors: Henri Doods, Warthausen (DE); Kirsten Arndt, Biberach (DE); Thierry Bouyssou, Warthausen (DE); Stephan Georg Mueller, Warthausen (DE); Klaus Rudolf, Warthausen (DE); Gerhard Schaenzle, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 254 days.

This patent is subject to a terminal disclaimer.

(21) Appl. No.: 11/760,057

(22) Filed: Jun. 8, 2007

(65) Prior Publication Data

US 2008/0139537 A1    Jun. 12, 2008

(30) Foreign Application Priority Data

Jun. 8, 2006   (EP) .................................. 06011787

(51) Int. Cl.
*A61K 31/551* (2006.01)
(52) U.S. Cl. .................................................. 514/221
(58) Field of Classification Search ........................ None
See application file for complete search history.

(56) References Cited

U.S. PATENT DOCUMENTS

| 7,479,488 | B2 | 1/2009 | Mueller et al. |
| 7,491,717 | B2 | 2/2009 | Mueller et al. |
| 7,528,129 | B2 | 5/2009 | Mueller et al. |
| 7,579,341 | B2 | 8/2009 | Mueller et al. |
| 7,582,625 | B2 | 9/2009 | Mueller et al. |
| 7,595,312 | B2 | 9/2009 | Rudolf et al. |
| 2004/0132716 | A1 | 7/2004 | Rudolf et al. |
| 2005/0234067 | A1 | 10/2005 | Mueller et al. |
| 2006/0252750 | A1 | 11/2006 | Mueller et al. |
| 2006/0252931 | A1 | 11/2006 | Mueller et al. |
| 2007/0244099 | A1 | 10/2007 | Rudolf et al. |
| 2009/0111797 | A1 | 4/2009 | Mueller et al. |
| 2009/0176770 | A1 | 7/2009 | Mueller et al. |
| 2009/0186881 | A1 | 7/2009 | Mueller et al. |
| 2009/0253680 | A1 | 10/2009 | Mueller et al. |

FOREIGN PATENT DOCUMENTS

| CA | 2503455 | A1 |   | 5/2004 |
| CA | 2503462 | A1 |   | 5/2004 |
| CA | 2558889 | A1 |   | 10/2005 |
| CA | 2600909 | A1 |   | 3/2006 |
| CA | 2600189 | A1 |   | 9/2006 |
| CA | 2618834 | A1 |   | 2/2007 |
| CA | 2623156 | A1 |   | 4/2007 |
| EP | 1770087 |    | * | 4/2007 |
| WO | 2004037810 | A1 |   | 5/2004 |
| WO | 2004037811 | A1 |   | 5/2004 |
| WO | 2005041757 | A2 |   | 5/2005 |
| WO | 2005092880 | A1 |   | 10/2005 |
| WO | 2006100009 | A1 |   | 9/2006 |
| WO | 2006100026 | A1 |   | 9/2006 |
| WO | 2007020261 | A2 |   | 2/2007 |
| WO | 2007036532 | A2 |   | 4/2007 |

OTHER PUBLICATIONS

International Search Report (Form PCT/ISA/220) for corresponding PCT/EP2007/055543.

* cited by examiner

*Primary Examiner*—Phyllis G. Spivack
(74) *Attorney, Agent, or Firm*—Michael P. Morris; Mary-Ellen M. Devlin; Alan R. Stempel

(57) ABSTRACT

The invention relates to a method for treating irritable bowel syndrome through the use of effective amounts of a compound acting as CGRP antagonist.

1 Claim, No Drawings

CGRP ANTAGONISTS

The invention relates to a method for preventing and treating visceral pain and gastrointestinal disorders such as functional bowel disorders and inflammatory bowel diseases through the use of effective amounts of a compound acting as CGRP antagonist.

BACKGROUND OF THE INVENTION

Technical Field

The viscera encompasses the organs of the abdominal cavity. Pain associated with the viscera can be divided into digestive visceral pain and non digestive visceral pain. Commonly encountered gastrointestinal disorders include the functional bowel disorders and the inflammatory bowel diseases. These gastrointestinal disorders include a wide range of disease states that are currently only moderately controlled, including gastro-esophageal reflux, dyspepsia, the irritable bowel syndrome and functional abdominal pain syndrome, Crohn's disease, ileitis and ulcerative colitis, and all regularly produce visceral pain.

Irritable bowel syndrome (IBS), also termed "irritable colon", "spastic colon" or "mucous colitis", is characterized by lower abdominal discomfort or pain associated with disturbance of defecation. The nature of the symptoms can vary between patients, varying from predominant constipation or diarrhoea to predominant pain.

It is the most common chronic gastrointestinal disorder, affecting about 20% of the world's population. This biopsychosocial disorder involves dysregulation of the nervous system, altered intestinal motility and increased visceral sensitivity.

All of these disorders result from dysregulation of the bidirectional communication between the gut with its enteric nervous system and the brain (the brain-gut axis), modulated by various psychosocial and environmental factors (e.g. infection, inflammation). Numerous neurotransmitters are found in the brain and gut that regulate GI activities, including 5-hydroxytryptamine (5-HT, serotonin) and its 5-$HT_3$ and 5-$HT_4$ receptors. The current approach to IBS patients is based on a positive diagnosis of the symptom complex, exclusion of underlying organic disease, and institution of a therapeutic trial. Traditional symptomatic treatment has included antidiarrheals, laxatives and bulking agents/fiber, low-dose tricyclic antidepressants, antispasmodics for pain, and 'alternative' therapies (e.g. psychotherapy, hypnotherapy).

The scientific evidence supporting this therapy is limited. Novel approaches include visceral analgesics and serotonin agonists and antagonists. In patients with severe diarrhea, 5-$HT_3$ receptor antagonists (e.g. alosetron) and selective $M_3$-type anticholinergics are indicated, in constipation 5-$HT_4$ agonists (e.g. tegaserod), and in pain $alfa_2$-adrenergics (e.g. clonidine), cholecystokinin antagonists, kappa-opioid agonists (e.g. fedotozine), and neurokinin antagonists; some of these agents are still being investigated. Understanding the brain-gut axis is crucial in the development of effective therapies for IBS (Med. Science Monit. 2004, 10(6), RA125-131).

Visceral hypersensitivity has been proposed as one of three underlying mechanisms of IBS and this is supported by the fact that patients suffering from IBS have enhanced perception of visceral events. This visceral hypersensitivity appears to be the result of sensitization of visceral afferent mechanisms, most likely peptidergic C-fibers. Those afferent C-fibers contain Calcitonin Gene Related Peptide (CGRP) and this peptide has been shown to be pronociceptive.

BRIEF SUMMARY OF THE INVENTION

It has now been found that the symptoms of IBS can be effectively prevented and their distressing effects substantially alleviated by substances which antagonise the effects of CGRP (CGRP antagonists) or inhibit or reduce the release of CGRP from sensory nerve endings (CGRP release inhibitors).

The present invention thus relates to the use of CGRP antagonists (A) and/or release inhibitors for combating IBS, including both prevention and active treatment. The use according to the present invention preferably comprises monotherapy with a single substance, but also includes combined therapy with a number of substances (B) from the specified groups of active substances.

The invention also relates to the use of CGRP antagonists and/or release inhibitors for preparing a pharmaceutical composition for the treatment of IBS as well as the corresponding pharmaceutical compositions containing as active substance one or more CGRP antagonists and/or release inhibitors.

Any pharmaceutically acceptable active substances which antagonise the known effects of CGRP or inhibit the release of CGRP from sensory nerve endings may be used for the purposes of the present invention.

DETAILED DESCRIPTION OF THE INVENTION

Examples of CGRP antagonists include the amino acid derivatives described in the international patent application PCT/EP97/04862, as well as the non-peptidic active substances described in international patent applications PCT/EP03/11762, PCT/EP03/11763, PCT/EP2004/000087, PCT/EP2005/003094, PCT/US03/16576, PCT/US2004/040721, PCT/US2003/038799, PCT/US2005/010330, PCT/GB99/03154, PCT/US2004/007226, PCT/US2004/007289, PCT/US2004/007686, PCT/US2004/007678, PCT/US2004/007715, PCT/US2004/011254, PCT/US2004/010851, PCT/US2004/011280, PCT/US2004/020206, PCT/US2004/021888, PCT/US2004/020209, PCT/US2005/002199, PCT/US2005/031713, PCT/US2005/031617, PCT/US2005/031712, PCT/US2005/032036, PCT/US2005/032041, PCT/US2005/032288, PCT/US2005/035654 and US 2006/0094707.

Examples of CGRP release inhibitors include serotonin 5-$HT_{1D}$-agonists such as avitriptan, eletriptan, naratriptan, rizatriptan, sumatriptan or zolmitriptan, as well as 5-$HT_{1F}$-agonists or NPY-agonists.

Of the CGRP antagonists described above, the following compounds (A), for example, may be used for the treatment of IBS, for the preparation of a corresponding pharmaceutical composition and as an ingredient of a corresponding pharmaceutical composition.

A first object of the present invention is therefore the use of a CGRP antagonist (A), selected from the group consisting of

| Number | Structure |
|---|---|
| (1) | 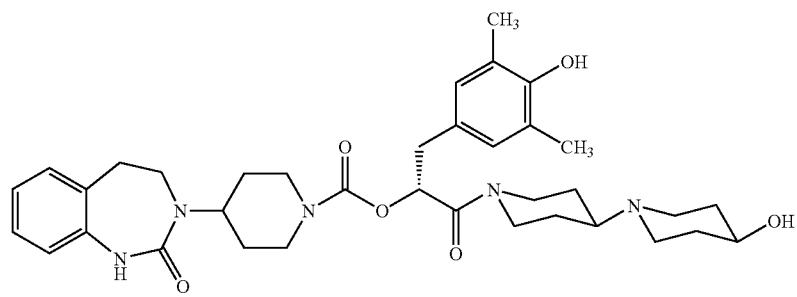 |
| (2) | 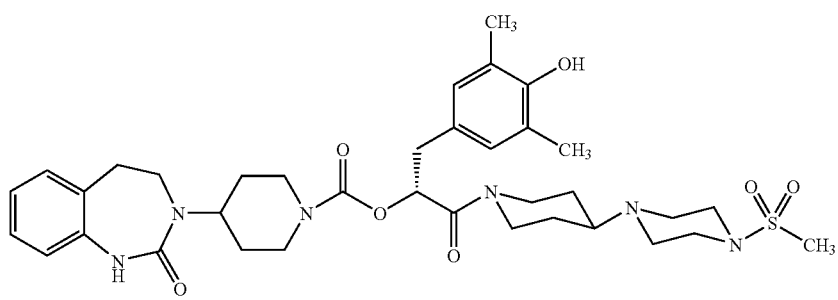 |
| (3) | 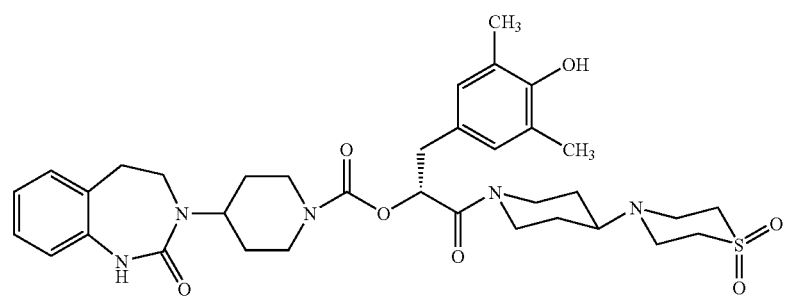 |
| (4) | 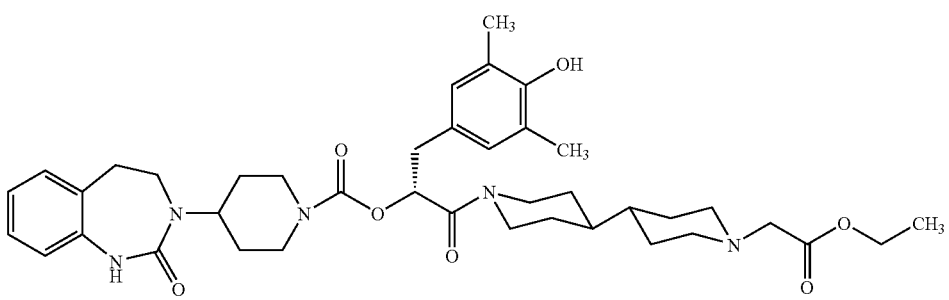 |
| (5) | 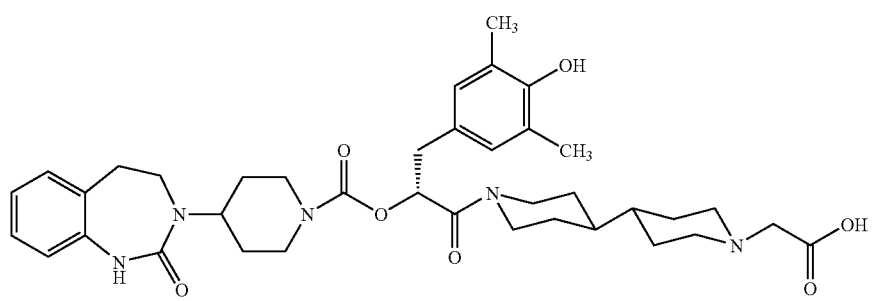 |

-continued
| Number | Structure |
|---|---|
| (6) | 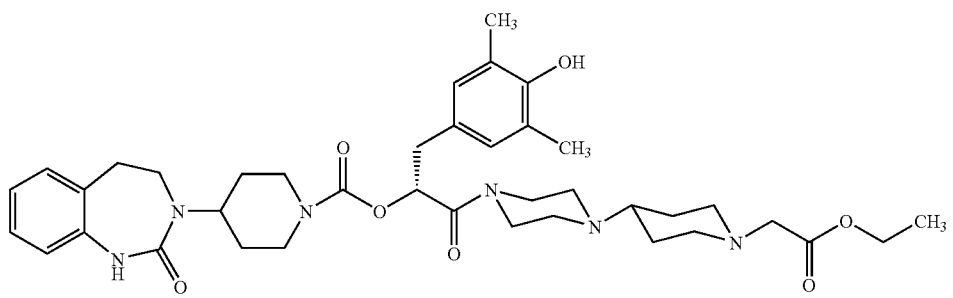 |
| (7) | 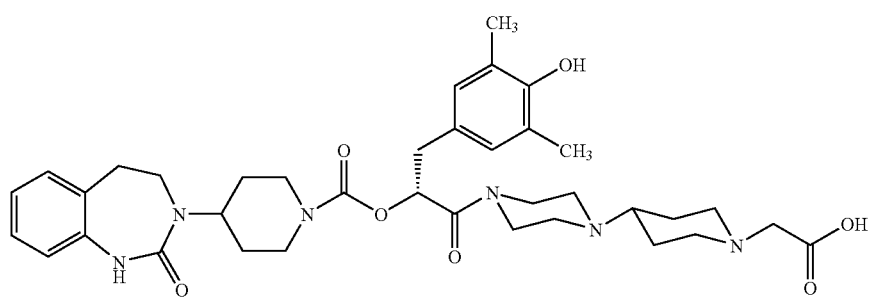 |
| (8) | 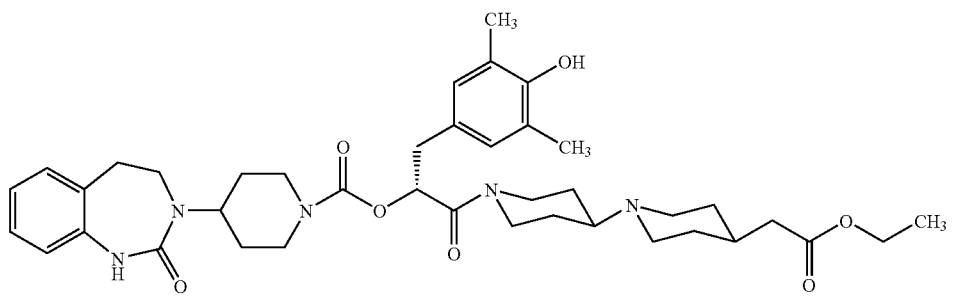 |
| (9) | 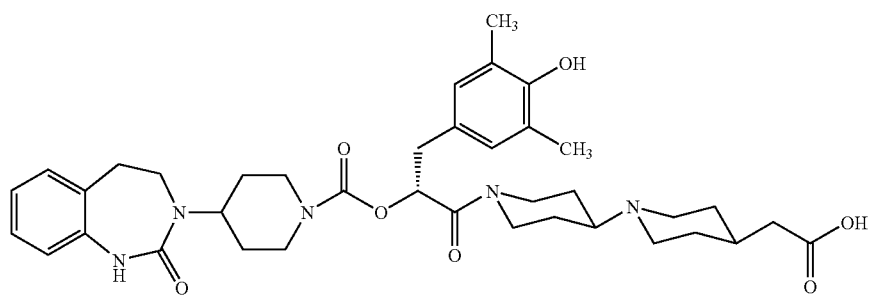 |
| (10) | 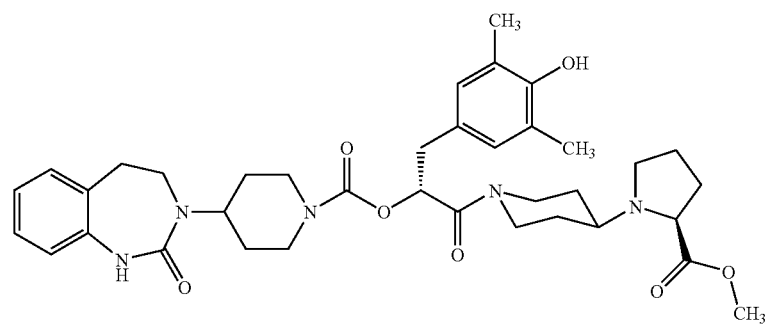 |

| Number | Structure |
|---|---|
| (11) | 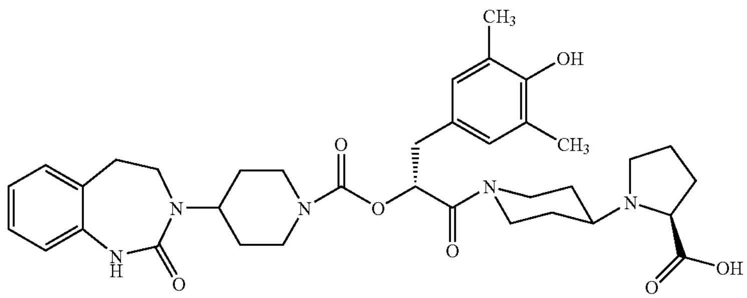 |
| (12) | 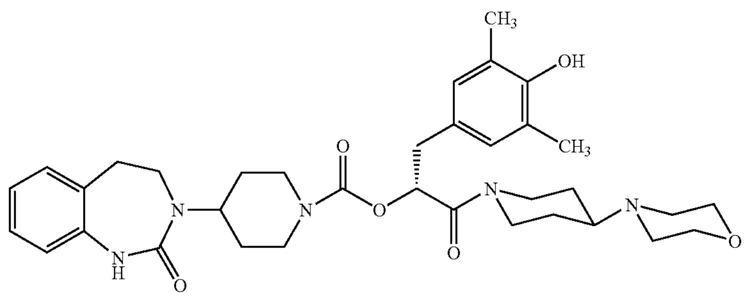 |
| (13) | 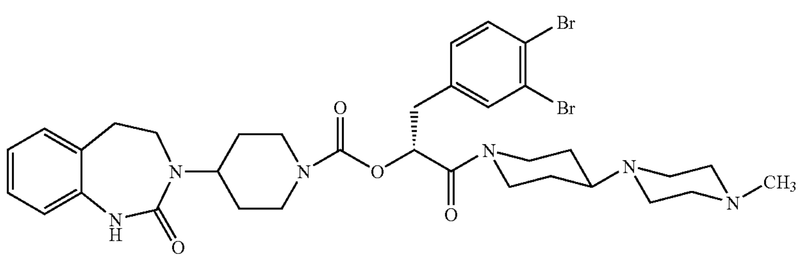 |
| (14) | 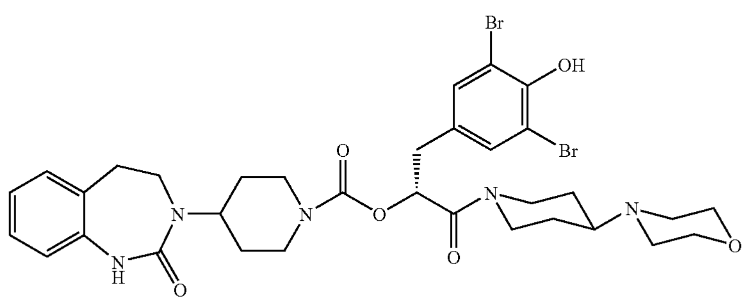 |
| (15) | 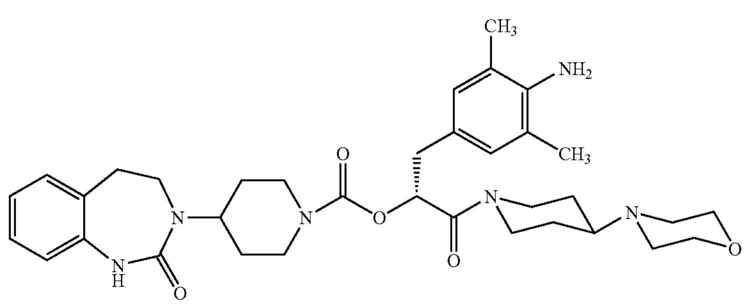 |

-continued
| Number | Structure |
|---|---|
| (16) | 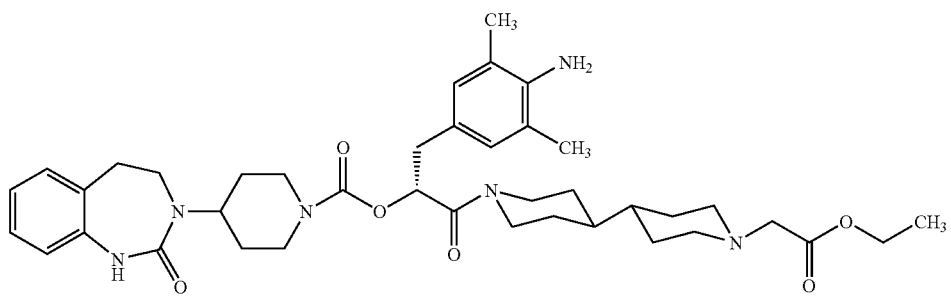 |
| (17) | 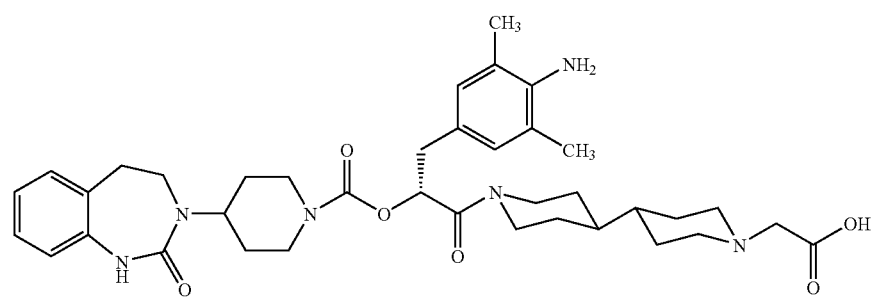 |
| (18) | 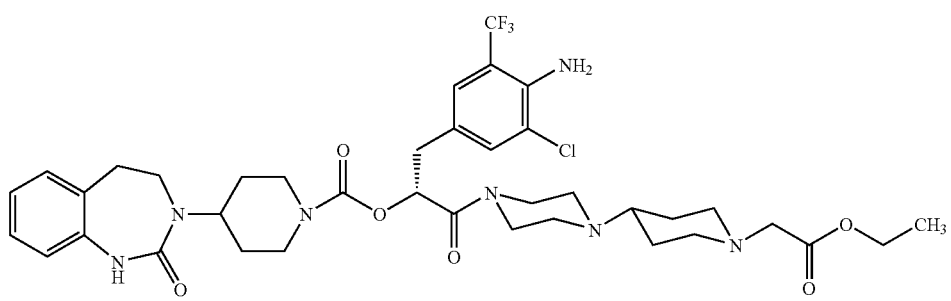 |
| (19) | 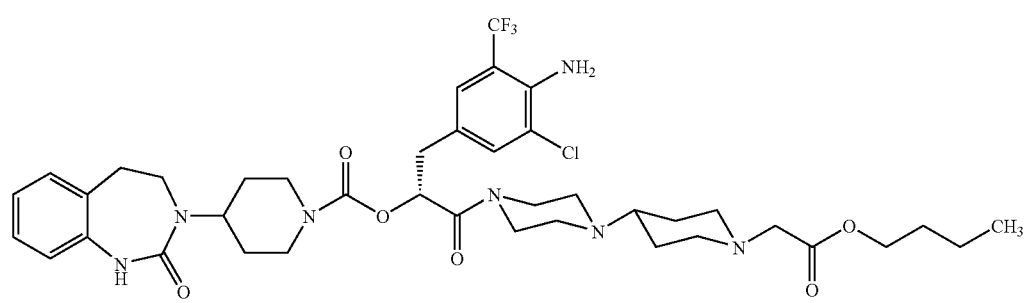 |
| (20) | 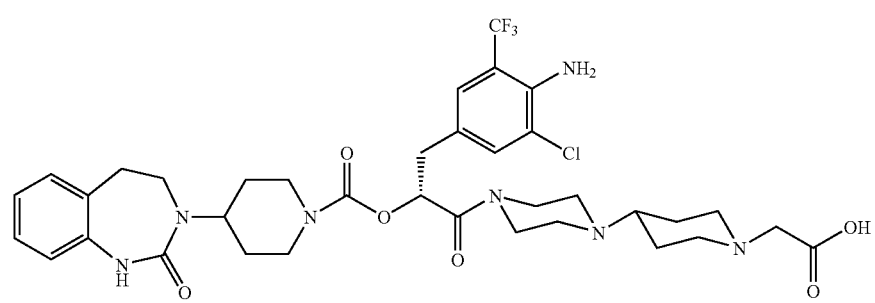 |

-continued
| Number | Structure |
|---|---|
| (21) | 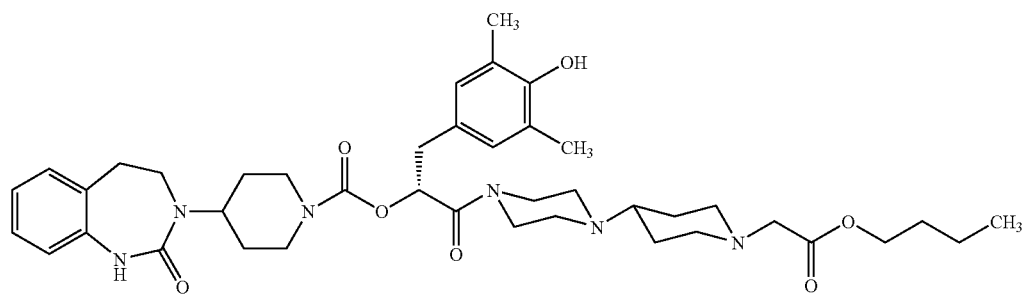 |
| (22) | 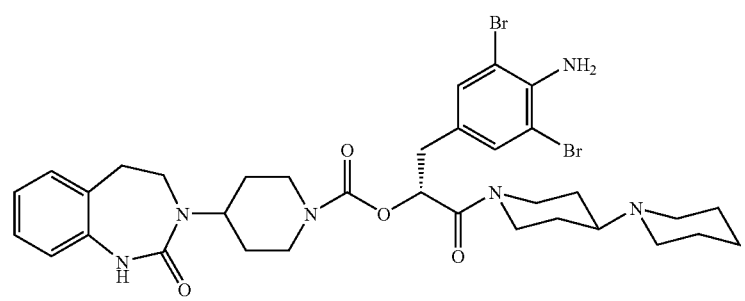 |
| (23) | 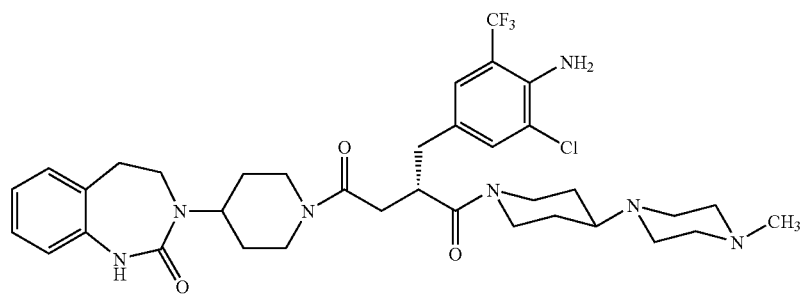 |
| (24) | 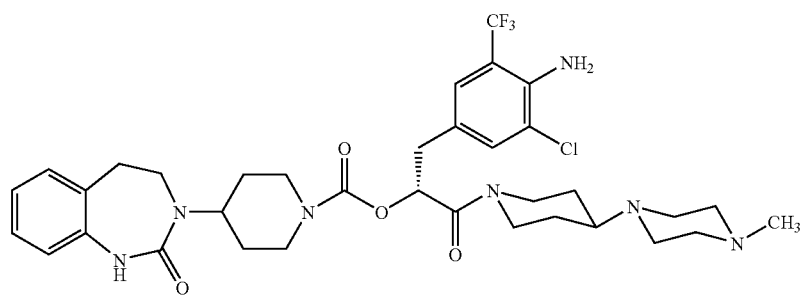 |
| (25) | 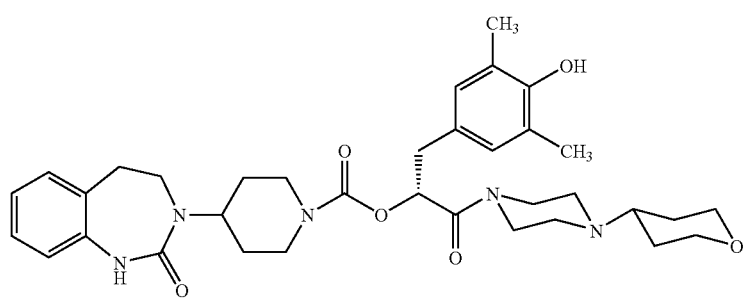 |

-continued

| Number | Structure |
|---|---|
| (26) | 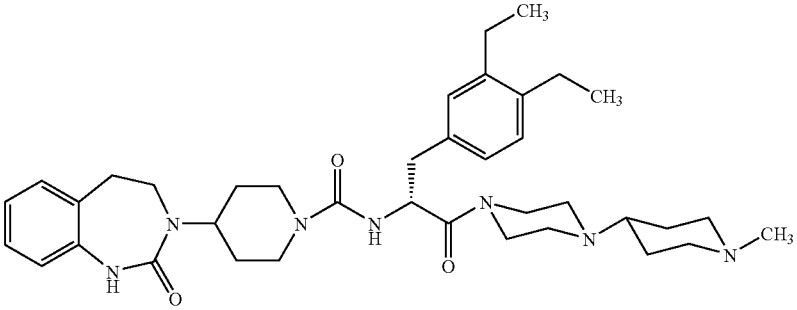 |
| (27) | 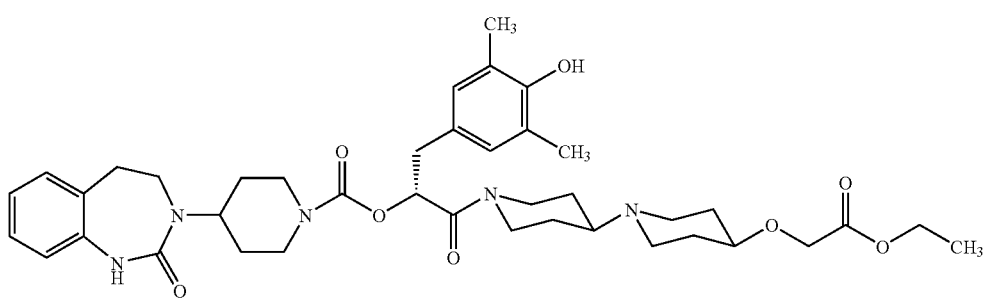 |
| (28) | 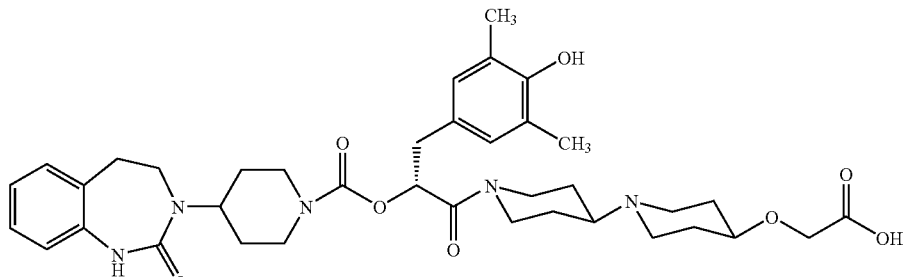 | the enantiomers, the diastereomers, the mixtures and the salts thereof, especially the pharmaceutically acceptable salts with organic or inorganic acids or bases, for the preparation of a pharmaceutical for the treatment of IBS in one of the following pharmaceutical formulations:

capsules for powder inhalation containing 1 mg of active substance (A), inhalable solution for nebulisers containing 1 mg of active substance (A), propellant gas-operated metering aerosol containing 1 mg of active substance (A), nasal spray containing 1 mg of active substance (A), tablets containing 20 mg of active substance (A), capsules containing 20 mg of active substance (A), aqueous solution for nasal application containing 10 mg of active substance (A), aqueous solution for nasal application containing 5 mg of active substance (A), suspension for nasal application containing 20 mg of active substance (A).

The specific mentioned compounds (A) according to the present invention are described in the international patent applications PCT/EP97/04862 and PCT/EP2005/003094 and can be prepared according to processes described in said applications.

The compounds were applied orally and are active in the dose range of 0.01 to 100 mg/kg.

TERMS AND DEFINITIONS USED

Also included in the subject matter of this invention are the compounds according to the invention, including the salts thereof, in which one or more hydrogen atoms, for example one, two, three, four or five hydrogen atoms, are replaced by deuterium.

The compounds according to the present invention may have acid groups, mainly carboxyl groups, and/or basic groups such as e.g. amino functions. The compounds according to the invention may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, for example sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

As mentioned hereinbefore, the compounds according to the invention may be converted into the salts thereof, particularly for pharmaceutical use, into the physiologically and pharmacologically acceptable salts thereof. These salts may on the one hand be in the form of the physiologically and pharmacologically acceptable acid addition salts of the compounds of formula I with inorganic or organic acids. On the other hand, if they contain a phenolic OH group, the compound according to the invention may also be converted by reaction with inorganic bases into physiologically and pharmacologically acceptable salts with alkali or alkaline earth metal cations as counter ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. The alkali and alkaline earth metal salts of the compound of formula I are preferably the alkali and alkaline earth metal hydroxides and hydrides thereof, of which the hydroxides and hydrides of the alkaline earth metals, particularly of sodium and potassium, are preferred and sodium and potassium hydroxide are particularly preferred.

The compounds according to the invention may occur as racemates if they have only one chiral element, but they may also be obtained as pure enantiomers, i.e. in the (R) or (S) form. Preferred compounds are those which occur as racemates or as the (R) form.

However, the application also includes the individual diastereomeric pairs of antipodes or the mixtures thereof which are present when there is more than one chiral element in the compounds according to the invention, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

Combinations

As mentioned above the CGRP antagonists (A) according to the present invention can be used as monotherapy, but can also used in combination with other active compounds (B) for the treatment of IBS.

For this purpose, the compound (B) can be selected from the group consisting of 5-HT1 agonist such as, 5-HT$_3$ antagonists, 5-HT$_4$ agonists, mixed 5-HT$_3$ antagonists/5-HT$_4$ agonists, serotonin norepinephrine reuptake inhibitors, antispasmotic agents, anticholinergics, laxatives, ballast, antidiarrheals, tricyclic antidepressants and SSRIs, opioids, local anaesthetics, alpha2 agonists, cannabiniods, P2X3/P2X2/3 antagonists, CCK-antagonists, VR-1/TRPV1 antagonists, neurokinin antagonists, beta-3 adrenoceptor agonists, NSAIDs, COX 2 inhibitors and probiotics which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

A 5-HT$_1$ agonist may be selected from the group consisting of avitriptan, eletriptan, naratriptan, rizatriptan, sumatriptan or zolmitriptan or the pharmaceutically acceptable salts thereof.

A 5-HT$_3$ antagonist may be selected from the group consisting of alosetron, cilansetron, granisetron or the pharmaceutically acceptable salts thereof.

A 5-HT$_4$ agonist may be selected from the group consisting of tegaserod, prucalopride or the pharmaceutically acceptable salts thereof.

A mixed 5-HT$_3$ antagonist/5-HT$_4$ agonist may be selected from the group consisting of renzapride, cisapride or the pharmaceutically acceptable salts thereof.

A serotonin norepinephrine reuptake inhibitor may be selected from the group consisting of venlafaxine, duloxetine and milnacipran or the pharmaceutically acceptable salts thereof.

An antispasmotic agent may be selected from the group consisting of pinaverium, mebeverine, alverine or the pharmaceutically acceptable salts thereof.

An anticholinergic may be selected from the group consisting of zamifenacin, darifenacin or the pharmaceutically acceptable salts thereof.

A laxative may be selected from the group consisting of lactulose and polyethylene glycol.

A ballast may be selected from the group consisting of methylcellulose and psyllium.

An antidiarrheal may be selected from the group consisting of loperamide, cholestyramine or the pharmaceutically acceptable salts thereof.

A tricyclic antidepressant and SSRI may be selected from the group consisting of amitriptyline, imipramine or the pharmaceutically acceptable salts thereof.

An opioid may be selected from the group consisting of fedotozine, trimebutine or the pharmaceutically acceptable salts thereof.

A local anaesthetic may be selected from the group consisting of trimebutine or the pharmaceutically acceptable salts thereof.

An alpha2 agonist may be selected from the group consisting of clonidine or the pharmaceutically acceptable salts thereof.

A cannabiniod may be selected from the group consisting of remonabant or the pharmaceutically acceptable salts thereof.

A neurokinin antagonist may be selected from the group consisting of ezlopitant, nepadulant or the pharmaceutically acceptable salts thereof.

A beta3-adrenoceptor agonist may be selected from the group consisting of solabegron or YM178 or the acceptable pharmaceutically acceptable salts thereof.

A NSAID may be selected from the group consisting of acclofenac, acemetacin, acetylsalicylic acid, azathioprin, celecobix, diclofenac, diflunisal, fenbufen, fenoprofen, flurbiprofen, ibuprofen, indometacin, ketoprofen, leflunomid, lornoxicam, mefenamic acid, meloxicam, naproxen, phenylbutazon, piroxicam, sulfasalazin, zomepirac or the pharmaceutically acceptable salts thereof.

A COX 2 inhibitor may be selected from the group consisting of meloxicam, rofecoxib, valdecoxib, parecoxib, etoricoxib, celecoxib or the pharmaceutically acceptable salts thereof.

A probiotic may be bifidobacterium.

Formulations

The compounds prepared according to the invention may be administered either on their own or optionally in combination with other active substances for the treatment of migraine by intravenous, subcutaneous, intramuscular, intra-articular, intrarectal or intranasal route, by inhalation, topically, transdermally or orally, while aerosol formulations are particularly suitable for inhalation. The combinations may be administered either simultaneously or sequentially.

Suitable forms for administration include for example tablets, capsules, solutions, syrups, emulsions or inhalable powders or aerosols. The proportion of pharmaceutically active compound or compounds should be in the range from 0.1 to 90% by weight, preferably 0.5 to 50% by weight of the total composition, i.e. in amounts which are sufficient to achieve the dosage range mentioned hereinbefore.

The preparations may be given orally in the form of tablets, powders, powders in capsules (e.g. hard gelatine capsules), or as solutions or suspensions. When taken by inhalation the active substance combination may be administered as a powder, an aqueous or aqueous ethanolic solution or by means of a propellant gas formulation.

Preferably, therefore, pharmaceutical formulations are characterised in that they contain one or more compounds of formula I according to the preferred embodiments described hereinbefore.

It is particularly preferable if the compounds of formula I are administered orally, and it is most preferable if they are administered once or twice a day. Suitable tablets may be obtained, for example, by mixing the active substances with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring agent such as vanillin or orange extract. They may also contain suspension adjuvants or thickeners such as sodium carboxymethyl cellulose, wetting agents such as, for example, condensation products of fatty alcohols with ethylene oxide, or preservatives such as p hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium lauryl sulphate and talc may also be used to produce the tablets. In the case of aqueous suspensions the active substances may be combined with various flavour enhancers or colourings in addition to the abovementioned excipients.

Method of Treatment

The CGRP antagonists (A) according to the present invention are active in a model for visceral pain in rodents. In this model hypersensitivity is induced by colonic irritation (e.g. by butyrate, trinitrobenzene sulfonic acid or acetic acid instillation). Colorectal balloon distension was applied to induce pain behaviour e.g. abdominal contractions (see Bourdu et al., Gastroenterology 2005, 128, 1996-2008; Diop et al., J. Phamacol. Exp. Ther. 2002, 302, 1013-1022; Plourde et al. Am. J. Physiol. 1997, 273, G191-G196).

Since the compounds reverse the colonic hypersensitivity in the afore mentioned model it is claimed that the CGRP antagonists (A) according to the present invention can be used for the treatment of visceral pain/hypersensitivity especially abdominal pain in patients with IBS but also colic pain and dysmenorrhoea.

The invention claimed is:

1. A method for treating irritable bowel syndrome which comprises administering, to a host suffering from irritable bowel syndrome, a therapeutically effective amount of a compound selected from the group consisting of:

| Number | Structure |
|---|---|
| (1) | 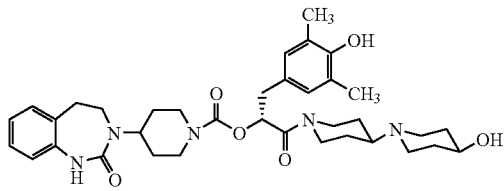 |

-continued
| Number | Structure |
|---|---|
| (2) | 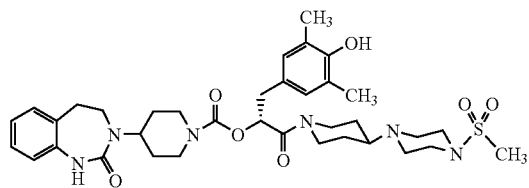 |
| (3) | 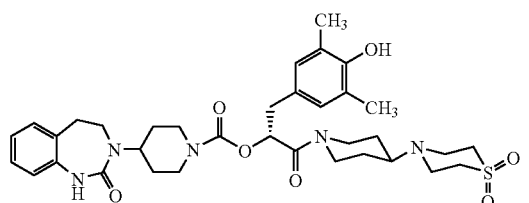 |
| (4) | 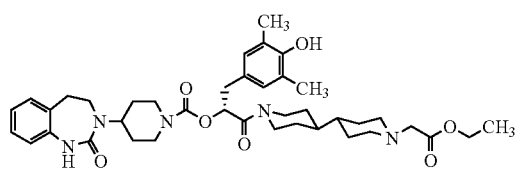 |
| (5) | 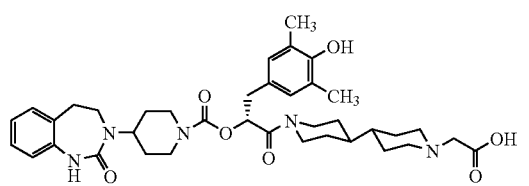 |
| (6) | 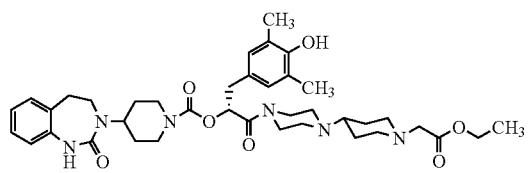 |
| (7) | 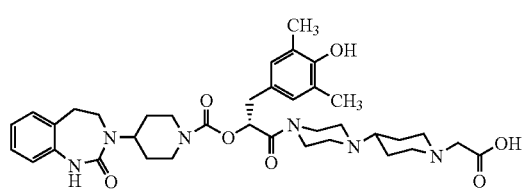 |
| (8) | 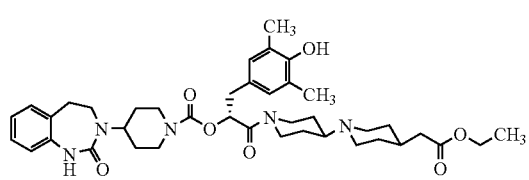 |
| (9) | 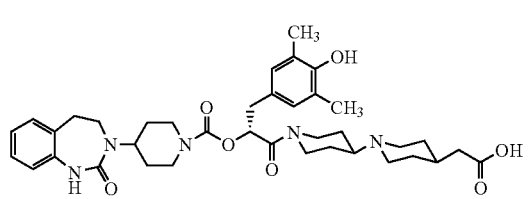 |
-continued
| Number | Structure |
|---|---|
| (10) | 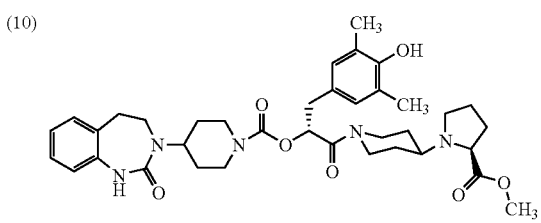 |
| (11) | 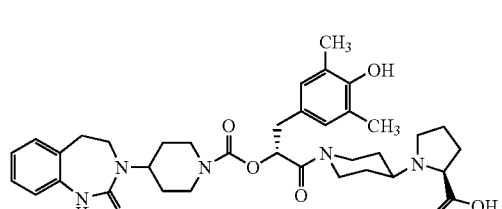 |
| (12) | 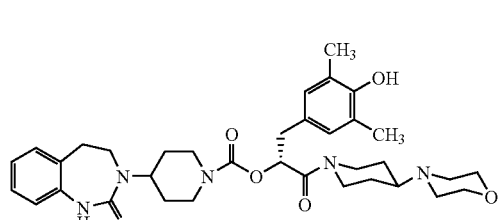 |
| (13) | 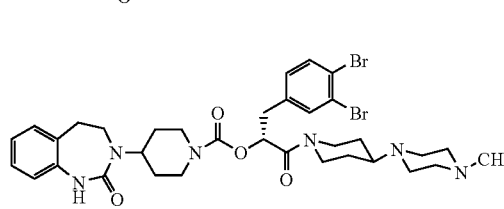 |
| (14) | 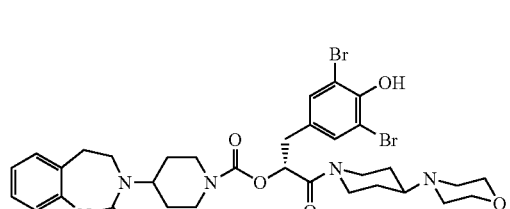 |
| (15) | 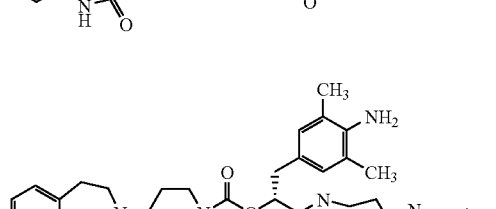 |
| (16) | 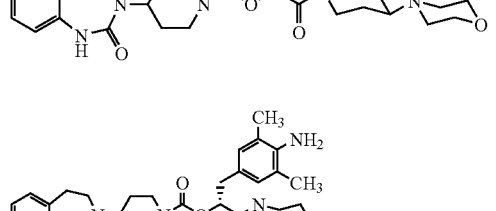 |

-continued
| Number | Structure |
|---|---|
| (17) | 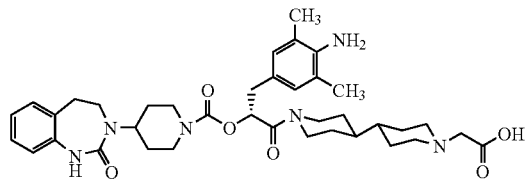 |
| (18) | 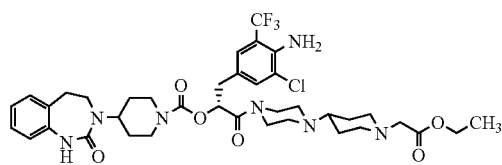 |
| (19) | 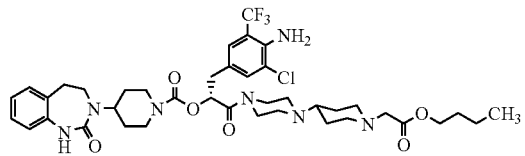 |
| (20) | 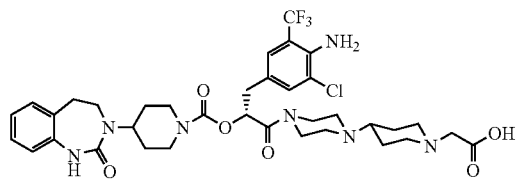 |
| (21) | 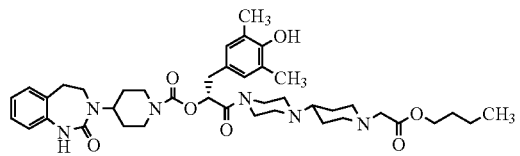 |
| (22) | 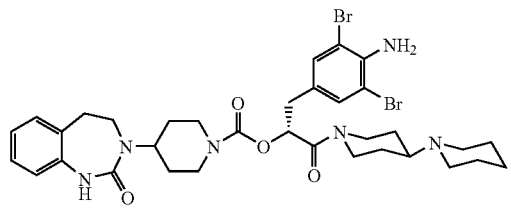 |
-continued
| Number | Structure |
|---|---|
| (23) | 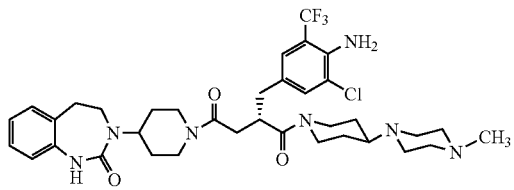 |
| (24) | 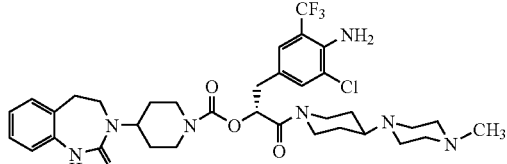 |
| (25) | 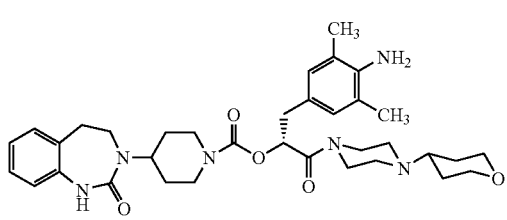 |
| (26) | 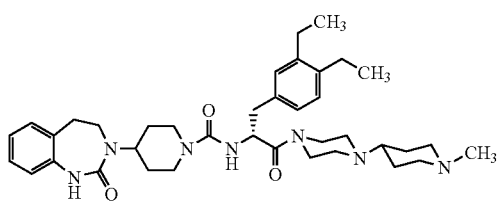 |
| (27) | 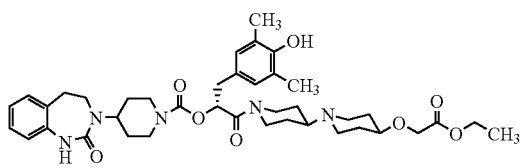 |
| (28) | 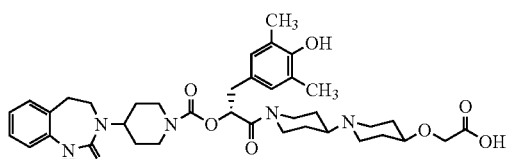 |
or a physiologically acceptable salt thereof.
\* \* \* \* \*